United States Patent [19]
Hagiwara et al.

[11] Patent Number: 5,429,802
[45] Date of Patent: Jul. 4, 1995

[54] MEDICAL INSTRUMENT

[75] Inventors: Kazuhiko Hagiwara; Hitoshi Kitoh, both of Shizuoka; Yoshihiro Oshibe; Hiroshi Ohmura, both of Aichi, all of Japan

[73] Assignee: Terumo Kabushiki Kaisha, Tokyo, Japan

[21] Appl. No.: 9,759

[22] Filed: Jan. 27, 1993

Related U.S. Application Data

[62] Division of Ser. No. 288,868, Dec. 23, 1988, Pat. No. 5,211,913.

[51] Int. Cl.$^6$ .............................................. A61M 1/14
[52] U.S. Cl. ........................................ 422/48; 422/44; 422/45
[58] Field of Search ....................... 422/44, 45, 46, 48

[56] References Cited

U.S. PATENT DOCUMENTS

| | | | |
|---|---|---|---|
| 4,020,230 | 4/1977 | Mahoney et al. | 264/210.4 X |
| 4,082,658 | 4/1978 | Fritzsche et al. | 210/500.23 X |
| 4,214,020 | 7/1980 | Ward et al. | 210/500.23 X |
| 4,239,729 | 12/1980 | Hasegawa et al. | 422/48 |
| 4,267,295 | 5/1981 | Gallop et al. | 526/264 |
| 4,374,802 | 2/1983 | Fukasawa | 422/48 |
| 4,376,095 | 3/1983 | Hasegawa | 422/48 X |
| 4,405,688 | 9/1983 | Lowery et al. | 264/177 X |
| 4,541,981 | 9/1985 | Lowery et al. | 264/209.1 |
| 4,620,965 | 11/1986 | Fukasawa et al. | 422/48 X |
| 4,639,357 | 1/1987 | Takemura et al. | 422/48 X |
| 4,659,549 | 4/1987 | Hamada et al. | 422/48 |
| 4,708,796 | 11/1987 | Yoshimoto et al. | 422/48 X |
| 4,715,953 | 12/1987 | Leonard | 422/48 X |
| 4,749,551 | 6/1988 | Borgione | 422/48 |
| 4,770,852 | 9/1988 | Takahara et al. | 422/48 |
| 4,781,889 | 11/1988 | Fukasawa et al. | 422/48 |
| 4,791,054 | 12/1988 | Hamada et al. | 422/48 |
| 4,923,679 | 5/1990 | Fukasawa et al. | 422/48 |
| 4,948,560 | 8/1990 | Deguchi et al. | 422/48 |
| 4,971,836 | 11/1990 | Fukasawa et al. | 422/48 X |
| 4,975,247 | 12/1990 | Badolato et al. | 422/48 |
| 5,037,610 | 8/1991 | Fukasawa et al. | 422/48 |
| 5,160,332 | 11/1992 | Nomura | 422/48 X |

FOREIGN PATENT DOCUMENTS

| | | |
|---|---|---|
| 005866 | 12/1979 | European Pat. Off. |
| 068509 | 1/1983 | European Pat. Off. |
| 292399 | 11/1988 | European Pat. Off. |
| 60-246762 | 12/1985 | Japan |
| 62-5173 | 2/1987 | Japan |
| 62-43565 | 11/1987 | Japan |

*Primary Examiner*—Donald E. Czaja
*Assistant Examiner*—Milton I. Cano
*Attorney, Agent, or Firm*—Burns, Doane, Swecker & Mathis

[57] ABSTRACT

The blood flow channel sections of an oxygenator and a blood resevoir are hydrophilized by treatment with an acid, an albumin solution, polyhydroxy methacrylate, corona discharge, plasma or ozone, so that it has highly improved wettability by the priming liquid and the blood to prevent blood foaming. The blood flow channel sections of a medical instrument may be additionally hydrophilized by treatment with a polymer containing hydroxyethyl methacrylate and methyl methacrylate or in addition thereto a poly(oxyethylene)-poly(oxypropylene) block polymer.

3 Claims, 4 Drawing Sheets

MEDICAL INSTRUMENT

This application is a divisional of application Ser. No. 07/288,868, filed Dec. 23, 1988 now U.S. Pat. No. 5,211,913.

BACKGROUND OF THE INVENTION

1. Field of the Invention

This invention relates to a blood reservoir or a hollow fibre type oxygenator in which the blood flow channel section of the blood reservoir or at least a fraction of the outer wall surfaces of the hollow fibre of the oxygenator is subjected to a chemical treatment such as with acid or albumin solutions or polyhydroxyethyl methacrylate, hereafter referred to as PHEMA, discharge treatment such as by corona or plasma treatment or with ozone and thereby hydrophilized to improve wettability thereof with the blood.

This invention also relates to medical implements or instruments in which the blood flow channel sections are hydrophilizingly treated using a polymer such as hydroxyethyl methacrylate (HEMA), methyl methacrylate (MMA) or using poly(oxyethylene)-poly(oxypropylene) block polymer after treated using above polymer.

2. Prior Art

Various polymers employed in the materials of medical implements are generally of hydrophobic properties. However, depending on usage and applications, not few of these materials require a hydrophilizing surface treatment.

In an oxygenator, for example, the housing is divided by a gas exchange membrane into two sections and a gas exchange is effected between the blood flowing in one of the, se sections and the gas, mostly oxygen, flowing in the other section. As a gas exchange membrane, polypropylene, polystyrene or silicone membranes, exhibiting hydrophobic properties are frequently employed.

It is noted that, before using the oxygenator, a priming operation is usually carried out to remove the air contained in the oxygenator. The membrane is hydrophobic and exhibits only poor affinity with water so that the air cannot be eliminated completely in the course of the printing operation. Above all, in the case of a hollow fibre type oxygenator employing porous hollow fibre as the gas exchange membrane, with the blood being caused to flow outside of the hollow fibre, there is demonstrated a strong tendency for the air to become trapped between the adjacent fibers of the hollow fibre. The result is that these adjacent fibers become flocculated by the air to form so-called cavities to lower the gas exchange performance.

The majority of the hollow fibre type oxygenators hitherto evolved were of the type in which the blood is caused to flow within the inside of the hollow fibre. However, because of large pressure losses encountered, it is felt that this type of the oxygenator can be applied to pulsed flow excorporeal circulation, separate excorporeal circulation or blood cardioplegia, only with considerable difficulties.

When the blood and the gas are caused to flow outside and inside of the hollow fibre, respectively, pressure losses may be lowered, so that the blood can be supplied to the oxygenator and thence to the blood reservoir by blood movement caused only by the pressure head from the patient's body without the necessity of providing a blood delivery pump ahead of the oxygenator in the circulating circuit. In this manner, the oxygenator can be adapted to blood cardioplegia or to separate excorporeal circulation.

With the hollow fibre formed by a hydrophobic resin, the fibre surface exhibits only low wettability by the blood, so that the blood cannot be distributed satisfactorily between the adjacent hollow fibre. Hence an effective gas exchange via the hollow fibre is obstructed and a sufficient gas exchange performance is not achieved. For wetting the outer wall surfaces of the hollow fibre, the air bubbles remaining between the hollow fibre need be removed by imparting a physical shock, such as by a laborious operation of striking the oxygenator.

In open heart surgery, a blood circuit with a built-in oxygenator is used in place of the living lung to eliminate carbon dioxide in the blood and to replenish oxygen in excorporeal circulation.

In the excorporeal blood circulation circuit with the built-in oxygenator, a blood reservoir is provided to eliminate air bubbles occasionally flowing into the circuit or to store and replenish the blood in the event of possible decrease in the blood circulation caused by, for example, tube rupture in the circuit.

In view of relative ease with which the stored blood quantity can be ascertained and the blood of a large volume can be stored, a hard shell type blood reservoir, formed of a hard material, is generally employed. Since the blood reservoir can then be incorporated easily into the oxygenator, there is proposed an oxygenator with a built-in blood reservoir.

However, when the blood reservoir exhibits hydrophobic properties, the blood or the priming liquid is not allowed to flow uniformly on the overall surface of the blood flow channel, but flows as a partialized flow into the blood reservoir to produce air bubbles.

The hard shell type blood reservoir 1 integrated to the oxygenator is shown diagrammatically in FIG. 1 and formed by a housing 7 formed of a hard material and including a blood inlet port 2, a blood influent section 5 communicating with the inlet port and presenting a bottom surface having substantially no drop from the inlet port 2, a blood reservoir section 6 communicating with the blood influent section and presenting a bottom surface gradually descending from the section 5 and a blood outlet 3 formed at the bottom of the reservoir section 6. It is noted that the bottom surfaces of the blood influent section 5 and the blood resevoir section 6 and the lateral sides of the housing 7 represent a blood flow channel surface.

The blood introduced via the blood inlet port 2 is caused to flow on the blood flow channel surface 4 so as to descend to and be stored in the blood storage section 6.

Heretofore, the housing 7 of the blood reservoir 1 was formed by a member of a material exhibiting hydrophobic properties, such as, for example, hard vinyl chloride resin, styrene resin or carbonate resin. As a result, the blood flow channel surface 4 also exhibited hydrophobic properties, so that, on performing bloodless priming, the priming liquid flow as a partialized flow without flowing uniformly on the overall blood flow channel surface 4. In this manner, the liquid flow will be disturbed and the priming liquid flows into the blood storage section 6 just like a fall flows down into a pond to produce the air bubbles or foam in the blood storage section 6. In addition, the above materials are not said to be satisfactory in compatibility to the blood.

It will be noted that the filter medium for removal of foreign matter of a blood filter or arterial filter provided downstream of the excorporeal circulating circuit is in the form of pleats, for elevating the properties of removal of foreign matter, so that air bubbles cannot be removed easily. Also, since the materials are hydrophobic, they are low in wettability, so that a certain pressure head is necessitated in the priming operation, which renders the priming operation difficult.

For combatting the above deficiency and improving wettability of the blood flow channel surface by the blood or the priming liquid, attempts have been made to hydrolyze the blood flow channel surface by a suitable surface treatment. However, these attempts have not met with success because of difficulties in simultaneously achieving uniform hydrophilic properties and improved compatibility to the blood without changing the properties of the material.

It is therefore an object of the present invention to provide an oxygenator in which the outer wall surface of the hollow fibre is hydrophilized to improve wettability thereof by the blood and the priming liquid to suppress formation of air bubbles without lowering the gas exchange properties.

It is another object of the present invention to provide a blood reservoir in which the blood flow channel surface is hydrophilized in part or in its entirety to improve wettability thereof by the blood and the priming liquid to suppress generation of air bubbles or foam by the blood flowing into the blood storage section.

The present invention has been fulfilled as a result of our perseverant researches for combatting the above deficiencies mainly caused by the hydrophobic properties of the blood flow channel sections of the medical instruments. It is an object of the present invention to provide a medical instrument in which at least the blood flow channel section thereof is subjected to a hydrophilizing treatment to improve wettability thereof by the blood or by the priming liquid to prevent affixture of air bubbles while simultaneously improving compatibility to the blood of the medical instrument.

The present invention has been fulfilled as a result of our perseverant researche for eliminating the above deficiencies mainly caused by the hydrophobic properties of the blood flow channel sections of the medical instrument. It is another object of the present invention to provide a medical instrument in which at least the blood flow channel section thereof is subjected to a hydrophilizing treatment to improve wettability thereof by the blood or by the priming liquid while simultaneously improving compatibility to the blood of the medical instrument.

DISCLOSURE OF THE INVENTION

According to a first aspect of the present invention, there is provided a hollow fibre type oxygenator in which the outer sides of the fibre are used as the blood flow channel, wherein at least some of said hollow fibres have the outer wall sides thereof hydrophilizingly treated so that air bubbles can be affixed to the outer wall sides of the hollow fibres only difficultly.

Preferably, the hollow fibre is a polyolefinic resin and the hydrophilizingly treated hollow fibre has such properties that the liquid surface is raised along the outer walls of the hollow fibre when one of the hollow fibres is introduced into water from a direction normal to the water surface.

According to a second aspect of the present invention, there is provided a blood reservoir comprising a blood flow channel surface inclined at least partially, a blood influent section located upstream of said blood flow channel surface, a blood storage section located below said blood flow channel surface, and a blood effluent section located downstream of said blood storage section, wherein said blood flow channel surface exhibit hydrophilic properties so that the blood introduced into the reservoir via the blood influent section and flowing down on the blood flow channel surface will flow substantially uniformly on the surface in its entirety without exhibiting the tendency to form a partialized flow on said surface.

The contact angle of the blood flow channel surface exhibiting the hydrophilic properties with respect to water is preferably less than 90° and more preferably not more than 80°.

According to a third aspect of the present invention, there is provided a medical instrument wherein at least the blood flow channel section thereof is coated in part or in its entirety by a polymer containing hydroxyethyl methacrylate (HEMA) and methyl methacrylate (MMA).

Preferably, hydroxyethyl methacrylate (HEMA) and methyl methacrylate (MMA) exist separately as respective separate segments. Preferably, the weight ratio of the segments containing hydroxyethyl methacrylate (HEMA) to the segments containing methyl methacrylate (MMA) is 50:50 to 95:5. More preferably, the content of hydroxyethyl methacrylate (HEMA) in said segment containing hydroxyethyl methacrylate (HEMA) is not less than 50 wt. % and the content of methyl methacrylate (MMA) in said segment containing methyl methacrylate (MMA) is not less than 70 wt. %.

Preferably, the medical instrument is an oxygenator and the blood flow channel section is the outer wall of porous hollow fibre housed within the oxygenator or a blood reservoir.

According to a fourth aspect of the present invention, there is provided a medical instrument wherein at least the blood flow channel section is coated in part or in its entirety by a polymer containing hydroxyethyl methacrylate (HEMA) and methyl methacrylate (MMA).

Preferably, hydroxyethyl methacrylate (HEMA) and methyl methacrylate (MMA) exist separately as respective separate segments.

Preferably, the weight ratio of the segments containing hydroxyethyl methacrylate (HEMA) to the segments containing methyl methacrylate (MMA) is 50:50 to 95:5. More preferably, the content of hydroxyethyl methacrylate (HEMA) in said segment containing hydroxyethyl methacrylate (HEMA) is not less than 50 wt. % and wherein the contents of methyl methacrylate (MMA) in said segment containing methyl methacrylate (MMA) is not less than 70 wt. %.

Additionally, after the medical instrument is treated by the polymer containing HEMA and MMA, it is treated by a poly(oxyethylene)-poly(oxypropylene) block polymer having the general formula

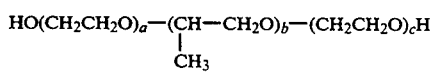

Preferably, a+c and b in the above formula are 2 to 2000 and 10 to 150, respectively.

Preferably, the medical instrument is an oxygenator and the blood flow channel section is the outer wall of porous hollow fibre housed within the oxygenator or a blood reservoir.

The medical instruments also include a blood reservoir and a blood filter.

The medical instruments further include components of a pump oxygenator such as the aforementioned pump oxygenator, blood reservoir or blood filter and a pump oxygenating circuit system formed by these components.

DETAILED DESCRIPTION OF THE INVENTION

A hollow fibre type oxygenator according to a first aspect and a blood reservoir according to a second aspect of the present invention will be described in detail with reference to a blood reservoir of the type to be built into the oxygenator according to a preferred embodiment of the present invention.

Figure 1:
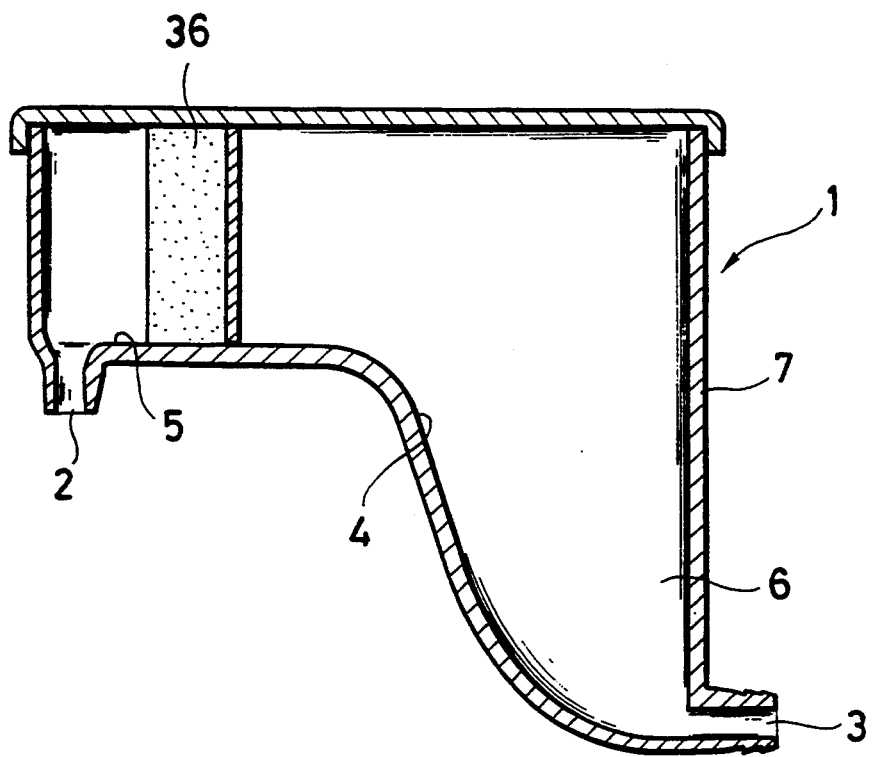
FIG. 1 is a longitudinal cross-sectional view showing an embodiment of a blood reservoir according to the present invention and a prior art device.

The hard shell type blood reservoir 1 incorporated to the oxygenator is shown diagrammatically in FIG. 1 and formed by a housing 7 formed of a hard material and including a blood inlet port 2, a blood influent section 5 communicating with the inlet port and presenting a bottom surface having substantially no drop from the inlet port 2, a blood reservoir or storage section 6 communicating with the blood influent section and presenting a bottom surface gradually descending from the section 5 and a blood outlet port 3 formed at the bottom of the reservoir section 6. It is noted that the bottom surfaces of the blood influent section 5 and the blood resevoir section 6 and the lateral sides of the housing 7 represent a blood flow channel surface 4.

The above described blood reservoir is provided within an excorporeal circulating circuit of the oxygenator. It is however more preferred that the blood reservoir be used as an oxygenating unit in which it is combined as one with the oxygenator and a heat exchanger, as shown for example in FIG. 2.

Figure 2:
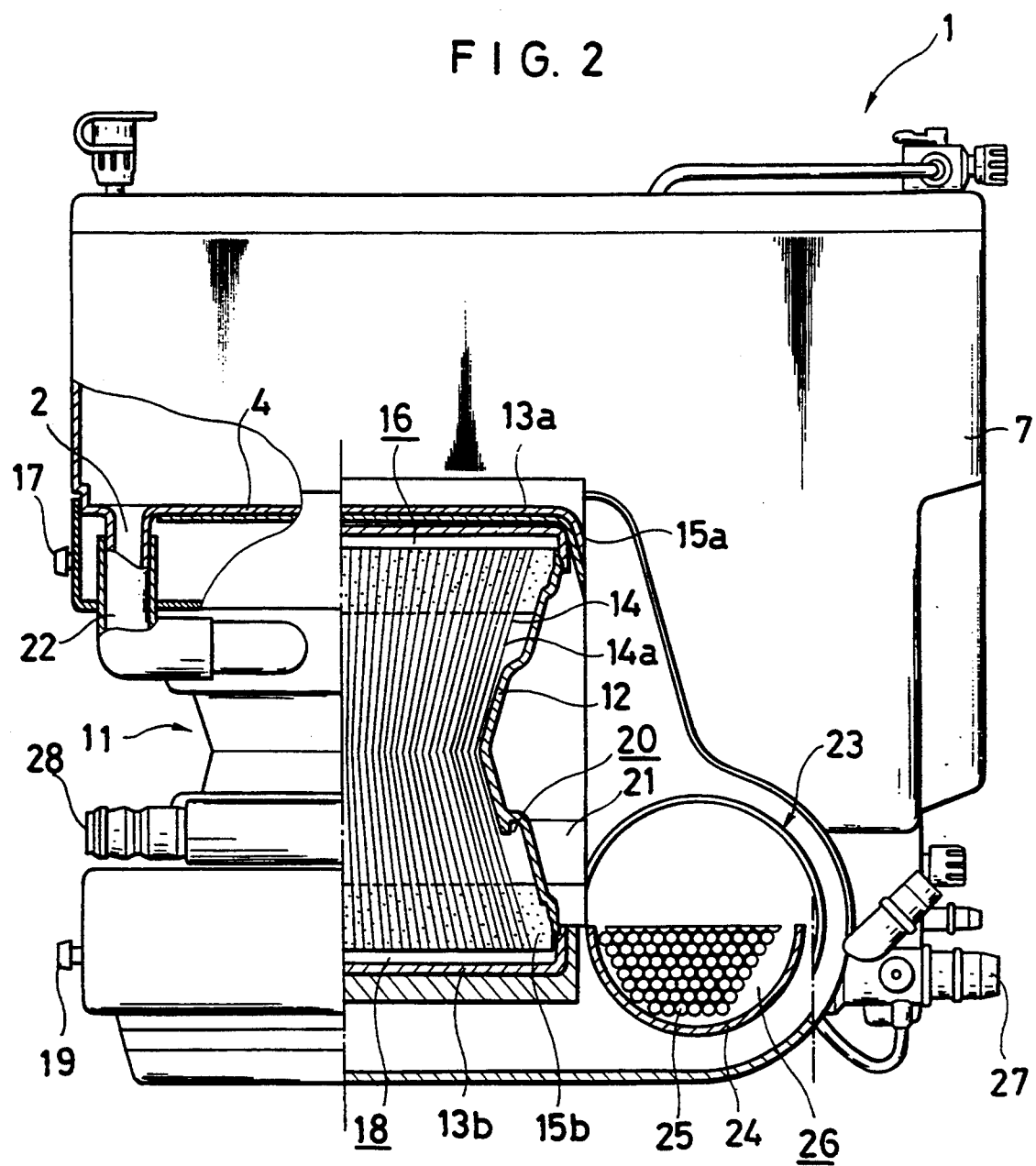
FIG. 2 is a front view, partially broken away and showing a pump oxygenator having hollow fibres according to the present invention.

In the preferred embodiment shown in FIG. 2, an oxygenator 11 includes a housing formed by a main body of the housing 12 and attachment covers 13a, 13b closing both open ends of the main body of the housing 12. There are provided within the housing a multiplicity of hollow fibres 14 parallel to and spaced apart from one another along the longitudinal direction of the housing.

These hollow fibres 14 are maintained liquid-tightly with respect to the main body of the housing 12 by partition walls 15a, 15b at the both ends with the ends of the fibres remaining open.

A gas inlet space 16 formed by the attachment cover 13a, main body of the housing 12 and the partition wall 15 so as to be in communication with the inner space of the hollow fibres communicates in turn with a gas inlet port 17, and a gas discharge space 18 formed by the attachment cover 13b, main body of the housing 12 and the partition wall 15b so as to be in communication with the inner space of the hollow fibres communicates in turn with a gas discharge port 19.

A blood chamber 20 defined by the inner wall of the main body of the housing 12, partition walls 15a, 15b and the outer walls of the hollow fibres 14 communicates with a blood inlet port 21 and a blood outlet port 22.

The oxygenator 11 shown herein is of the type in which gas exchange is performed with the oxygen-containing gas such as air being blown in the inner space of the hollow fibres 14 and with the blood being caused to flow on the outer sides of the hollow fibres 14.

The hollow fibres 14 may be formed of any suitable hydrophobic materials customarily used for oxygenators. For example, polytetrafluoroethylene, polypropylene or silicone is preferred.

To the blood outlet 22 of the oxygenator 11, there is connected liquid-tightly the blood inlet port 2 of the blood reservoir 1 described with reference to FIG. 1.

A heat exchanger 23 is connected to the blood outlet 21 of the oxygenator 11. The heat exchanger 23 includes a casing 24 in which a multiplicity of heat exchanger tubes 25 are arranged parallel to and at a spacing from one another along the length of the casing 24. The both ends of the heat exchanger tubes 25 are held liquid-tightly with respect to the side walls of the casing 24 by partition walls, not shown, with the opening ends of the tubes remaining open.

A spacing 26 defined by these partition walls, side walls of the casing 24 and the outer walls of the heat exchanger tubes 25 is kept in communication with a blood inlet port 27 and the blood inlet 21 to the oxygenator 11. The inner spacing of the heat exchanger tubes 25 liquid-tightly separated from the spacing 26 is kept in communication with a water inlet port 28 communicating with the outer side of one of the partition walls of the casing 24 and a water outlet port, not shown, communicating with the outer side of the other partition wall of the casing 24.

In the above described heat exchanger 23, the blood flows into the heat exchanger 23 via blood inlet port 27 to flow along the outer sides of the heat exchanger tubes 25, while warm or cold water flows in the inside of the heat exchanger tubes 25 to warm or chill the blood contacting with the heat exchanger tubes 15. However, it is also possible to use a heat exchanger of the type in which the blood flows in the inside of the heat exchanger tubes and the cooling or heating medium is caused to flow in the outer sides of the heat exchanger tubes.

It is an important feature of the present invention that part or all of the blood flow channel surface from the blood inlet 21 to the blood outlet 22 in the above exemplified oxygenator on which the blood is likely to contact with oxygenator components, especially the hollow fibres, is subjected to a hydrophilizing treatment. It is not always necessary that the totality of the hollow fibres making up the hollow fibre bundle be hydrophilized. For example, more than half the hollow fibres may be hydrophilized and arrayed uniformly alternately with the remaining unhydrophilized fibres. In the event that the central portion of the hollow fibre bundle is constricted and throttled axially by the housing of the oxygenator, it suffices that at least this constricted portion be hydrophilized.

According to the present invention, as already described with reference to the blood resevoir exemplified in FIG. 1, all or part of the blood flow channel surface of the blood reservoir exhibits hydrophilic properties. It may be the material constituting the blood flow channel surface itself that exhibits these properties.

There are a number of methods of hydrophilizing the blood flow channel surface. The following summarizes some of these methods that may be employed in connection with the present invention.

(1) Acid Treatment

The acids that may be employed include $KM_nO_4/H_2SO_4$ and $K_2Cr_2O_4/H_2SO_4$ solutions. Above all, the $KM_nO_4/H_2SO_4$ solution is preferred. For hydrophilizing treatment, the concentrations of 0.05 to 1 wt. % of $KM_nO_4$ and 90 to 100 wt. % of $H_2SO_4$ are preferred as the concentrations of the components of the above solution.

In addition to the above acid mixtures, acids such as $H_2SO_4$ may be used alone.

(2) Treatment with an Albumin Aqueous Solution

An albumin aqueous solution of 0.5 to 8 w/v % may be conveniently employed for hydrophilizing treatment.

(3) Treatment with PHEMA

This is the treatment with PHEMA or polyhydroxyethyl methacrylate. For the intended hydrophilizing treatment, the concentration of 0.05 to 4 wt. % is preferred.

(4) Corona Discharge Treatment

In the corona discharge treatment, the corona discharge is caused to occur on a material to introduce hydrophilic groups on the material surface. The duration of processing is set in dependence upon the degree of the required hydrophilization.

(5) Plasma Treatment

In plasma processing, active species produced by the glow discharge are used to treat the polymer surface. The duration of processing is again set in dependence upon the degree of hydrophilization required.

(6) Ozone Treatment

In the ozone treatment, ozone is caused to occur on a material to introduce hydrophilic groups on the material surface. The duration of processing is set in dependence upon the degree of hydrophilization required.

As described above, various methods may be employed for hydrophilizing the oxygenator. For easiness of understanding, the degree of hydrophilization may be evaluated in terms of wettability by water.

A hollow fibre may be said to be endowed with hydrophilic properties when the water surface rises along the outer wall of the fibre introduced into water from the direction normal to the water surface.

When the fibre is not hydrophilized, that is, not subjected to a hydrophilizing treatment, the water surface becomes concave along the outer wall of the hollow fibre.

In a material by which the blood reservoir of the present invention is formed, a contact angle with water of not more than 90 degrees, preferably up to 80 degrees may endow satisfactory wettability with both priming solution and blood. Operation In the oxygenator unit shown in FIG. 2, in which the blood reservoir 1 is integrated with the oxygenator 11 and the heat exchanger, the blood flowing into heat exchanger 23 via blood inlet port 27 is heated or cooled until it arrives at the blood inlet port 21 of the oxygenator 11. The blood flowing into the oxygenator 11 via blood inlet 21 undergoes gas exchange with the oxygen-containing gas via hollow fibres 14 with the oxygen-containing gas circulated through the inside of the hollow fibres 14, as the blood flows through the blood chamber 20, such that carbon dioxide in the blood is removed while the consumed oxygen is replenished.

It is noted that, since the blood flow channel surface of oxygenator components, above all, preferably the overall surface of the outer walls 14a of the blood flow channel surface of the hollow fibre 14, is hydrophilized by the above described hydrophilizing treatment, for improving wettability by the blood, there is no risk that the fibers will be flocculated by the air to form cavities, as in the above described prior art. On the other hand, the blood may flow smoothly into the blood chamber 20 without stagnation so that the gas exchange may take place efficiently.

The blood thus replenished with oxygen exits at the blood outlet 22 of the oxygenator 11 to flow into the blood reservoir 1 via blood inlet port 2 of the blood reservoir 1. The blood thus introduced via blood inlet port 2 then reaches the blood influent section 5 communicating with the port 2 to flow smoothly on the blood flow channel surface 4 to flow down quietly into the blood reservoir section 6 for storage therein.

Heretofore, the housing 7 of the blood reservoir 1 was formed of a hydrophobic material, such as hard vinyl chloride resin, styrene resin or carbonate resin. For this reason, the blood flow channel surface presents hydrophobic properties. Thus, in the event of bloodless priming, the priming liquid does not flow on the overall surface of the blood flow channel surface 4, but flows unevenly, causing disturbances in the liquid stream. Thus an inconvenience is caused that the priming liquid flows into the blood reservoir section 6 as a waterfall drops into a pond so that the priming liquid forms bubbles in the blood reservoir section.

According to the present invention, the blood flow channel surface 4 of the blood reservoir 1 described with reference to FIG. 1 is hydrophilized by the above described methods of hydrophilizing treatment whereby the wettability of the channel surface by the blood and the priming, liquid is improved The blood and the priming liquid do not flow unevenly or at one time on the blood flow channel surface 4, but forms a uniform flow as a whole to prevent foaming.

The present invention will be explained further in connection with a medical instrument according to third and fourth embodiments of the invention.

According to the present invention, the material coating at least the blood flow channel section of the medical instrument in part or as a whole by way of a hydrophilizing treatment is preferably hydroxyethyl methacrylate (abbreviated hereafter to HEMA) and methyl methacrylate (abbreviated hereafter to MMA). It is because these polymers have a high degree of safety, adaptability to blood, bioadaptabilty and polymer synthesis and coating can be made easily.

It is preferred that the polymer containing HEMA and MMA be in the form of a block copolymer in which HEMA and MMA are bonded together as separate segments. It is also preferred that the segments exist separately in the polymer, since then the segments containing MMA exhibiting high water-proofness can be intimately bonded to the base material while the segments containing HEMA exhibiting hydrophilic properties can be disposed on the surface to provide for a surface hydrophilizing treatment having high degree of stability.

It is also preferred that the weight ratio of the HEMA containing segment, referred to hereafter as A segment, to the MMA containing segment, referred to hereafter as B segment, be 50:50 to 95:5. By the A segment and the B segment herein are meant those fragments or portions mainly containing HEMA and MMA, respectively. With the weight ratio of the A segment to B segment is less than 50:50, the hydrophilic properties on the surface are lowered. With a weight ratio in excess of 95:5, the coating polymer is likely to be eluted or peeled during usage.

It is also preferred that the contents of HEMA in the A segment be not lower than 50 wt. % and that the contents of MMA in the B segment be not lower than 70 wt. %. With a content of HEMA in the segment A less than 50 wt. %, the hydrophilic properties are lowered. With a content of MMA in the polymer less than 70 wt. %, tightness of bonding of the segment to the base material is lowered, depending on the properties of polymer components other than MMA.

It is noted that, according to the present invention, there is no specific limitation to the method of coating the polymer containing HEMA and MMA on the medical instrument and practically any method of coating may be employed.

Although a number of methods may be contemplated for preparing the polymer employed in the present invention, one may use a method including producing an acrylic polymer having peroxy bonds in the main chain (HEMA containing polymer) and effecting dispersion polymerization, using this polymer as the polymerization initiator, to produce a block copolymer with a MMA containing polymer.

According to a third aspect of the present invention, the medical instrument is preferably a porous hollow fibre housed within an oxygenator or a blood reservoir. In any case, at least the blood flow channel section thereof is coated in part or as a whole by the above described polymer to improve wettability by blood and adaptability or compatibility to blood.

Thus, in the blood reservoir, the polymer is coated mainly on the blood flow channel surface of the housing to render the flow of the priming liquid and the blood to the blood reservoir section more smooth. In the porous hollow fibre, one of the inner and outer walls of the hollow fibre is used in general as the blood flow channel surface. However, the present invention is applied to the hollow fibre, the outer wall of which, above all, is used as the blood flow channel surface. Thus the outer wall of the hollow fibre is coated with the above polymer to improve wettability by blood and to render the blood stream more smooth.

In this manner, adaptability to the blood of the hollow fibre may be improved simultaneously.

It is to be noted that portions other than the portions forming the blood flow channel surface may also be subjected to the above described hydrophilizing treatment.

According to a fourth aspect of the present invention, for improving wettability, after the blood flow channel section of the medical instrument is processed and coated with the above polymer containing HEMA and MMA, it is processed and treated with a poly(oxyethylene)-poly(oxypropylene) block polymer represented by the following general formula (I)

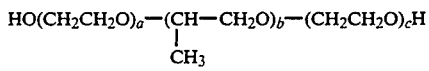

It is noted that there is no specific limitation to means of coating the medical instrument with the block copolymer and any known methods for coating may be employed.

In this manner, wettability and the properties of preventing foam deposition or affixture may be improved simultaneously. For obtaining the above results for the medical instrument of the present invention, a+c in the above is 2 to 2000, preferably 2 to 500 and more preferably 3 to 300, and b is 10 to 150, preferably 10 to 100 and more preferably 15 to 70. Outside of these ranges, hydrophilic properties of the block copolymer itself are lowered or the affinity to the hydrophobic section is lowered, so that wettability on the surface of the material following the processing is correspondingly lowered.

The medical instruments according to a fourth aspect of the present invention include those instruments and components thereof likely to come into contact with blood, such as in a circuit for cardiopulmonary by-pass, artificial dialysis system, blood plasma separating system and a variety of catheters. In the case of the circuit for cardiopulmonary by-pass, the medical instruments mean both the respective components making up the system and the system in its entirety. The components making up the system include an oxygenator, above all, a film or membrane type oxygenator, a blood reservoir, such as arterial reservoir, vena reservoir or cardiotomic reservoir, bubble trap, centrifugal pump and tubes connecting these components. In any of the above case, at least the blood flow channel sections of these components are coated in part or as a whole by the above polymer to improve wettability by blood, adaptability or compatibility to blood and the properties of preventing affixture of air bubbles.

That is to say, in the blood reservoir, the above polymer is coated mainly on the blood flow channel surface of the housing to render the flow of the blood and the priming liquid to the blood reservoir section more smooth. In the case of the porous hollow fibre within the oxygenator, one of the inner and outer walls of the hollow fibre is used as the blood flow channel surface. Especially, in the case or the hollow fibre the outer wall side of which is used as the blood How channel surface, the outer wall of the hollow fibre can be coated with the above polymer to improve wettability by blood to render the blood flow more smooth.

In this manner, the adaptability to blood of the hollow fibre is also improved simultaneously. In the case of the hollow fibre the inner wall of which is used as the blood flow channel surface, the inner wall of the fibre may also be coated with the above polymer to improve the properties of preventing formation of air bubbles and adaptability to blood.

It is to be noted that the portions of the hollow fibre other than those forming the blood flow channel surface may also be subjected to the above described hydrophilizing treatment.

Figure 3:
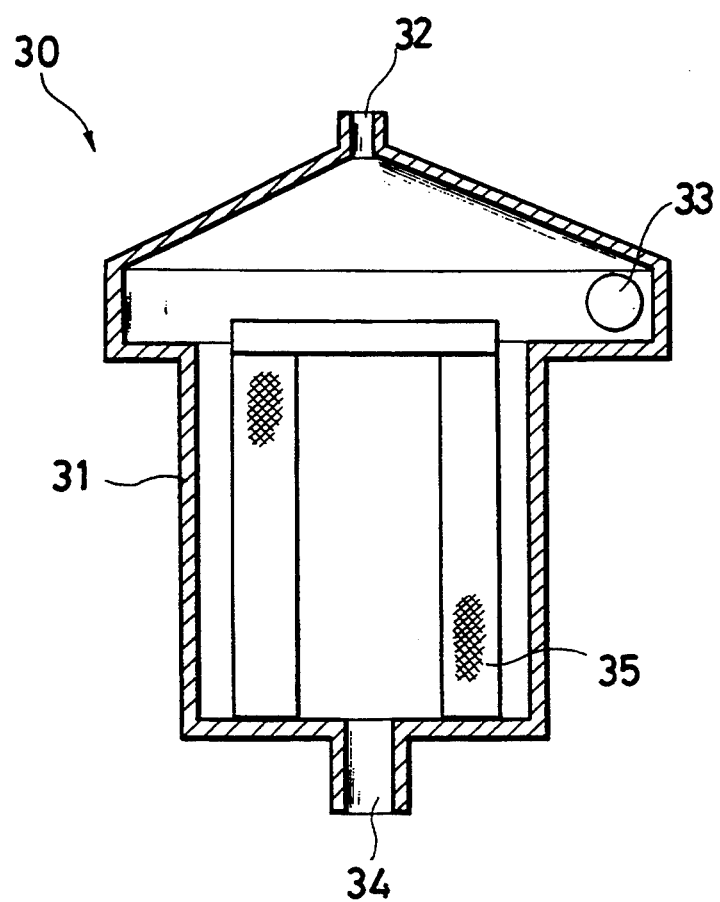
FIG. 3 is a cross-sectional view of a blood filter.

The medical instrument according to the present invention includes a blood flow filter 30 shown in cross-section in FIG. 3. This filter is incorporated into, for example, a pump oxygenating circuit to effect ultimate defoaming at the time the blood is returned into the patient's body.

The blood flow filter 30 has a housing 31 having an upper air discharge port 32, a central blood inlet port 33 and a lower blood outlet port 34.

A filter medium 35 formed by a polyester net is provided between the blood inlet port 33 and the blood outlet port 34.

The blood introduced into the blood inlet port 32 flows down the wall of the housing 31 as it gyrates to reach the filter medium 35. During this time interval, the blood defoamed by the filter material 35 is returned to the patient's body via outlet port 34, while the air removed from the blood is discharged via air outlet port 34.

Such blood filter is also preferably processed by a polymer containing HEMA and MMA or in addition thereto with the block copolymer represented by the above general formula (I), similarly to the blood reservoir or the pump oxygenator described above. In this manner, the defoaming properties are improved, while the priming time is reduced as a result of improved wettability. In a hard shell type blood reservoir, one or more components 36 in the form of a sponge and/or a net may be provided halfway in the blood flow channel for improving the defoaming efficiency and removal of impurities. In this case, only the aforementioned components or the blood reservoir including these components in its entirety may be processed by the above polymer to defoam the trapped air bubbles quickly.

Figure 4:
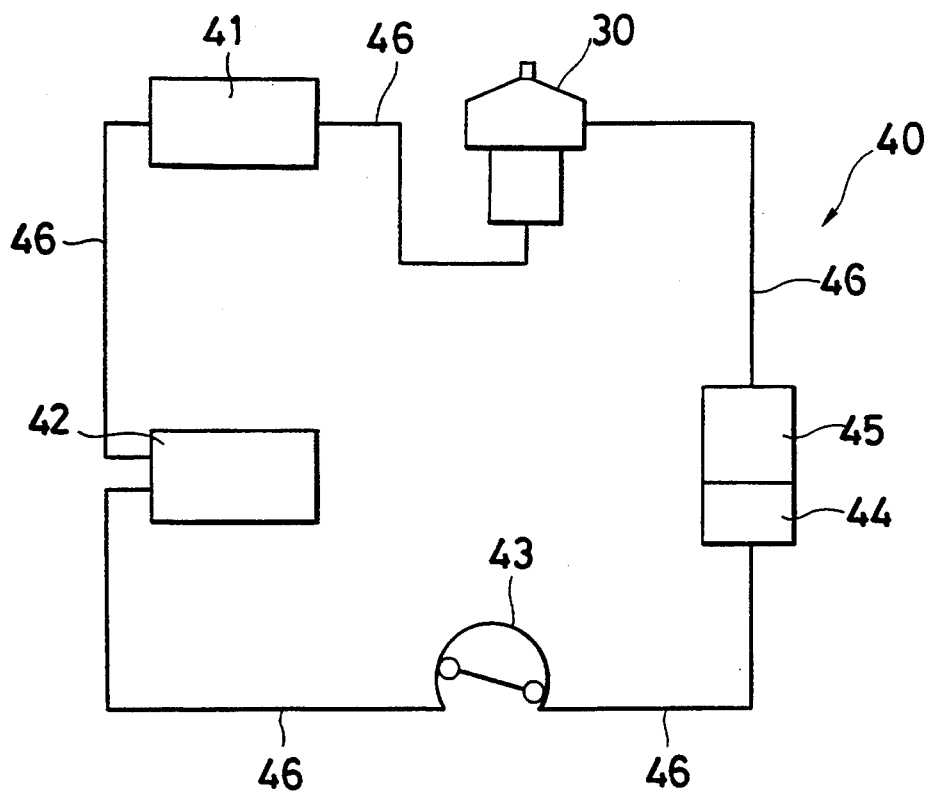
FIGS. 4 and 5 are diagrammatic views showing a pump oxygenating circuit system.

FIG. 4 shows an example of a pump oxygenating circuit system 40 including the aforementioned blood reservoir, pump oxygenator and blood filter. In this system the blood reservoir 42, pump 43, oxygenator 45 with a heat exchanger 44 and a blood filter 30 are interconnected with a human body 41 by a tube 46 to form an excorporeal circulating circuit.

Such circuit as a whole is preferably processed with the aforementioned polymers containing HEMA and MMA or with the block polymer represented by the general formula (I) to provide for improved wettability and the properties of preventing affixture of air bubbles.

OPERATION

The operation of an oxygenator including a blood reservoir and porous hollow fibres as the medical instrument of the present invention will be explained in more detail.

It is a feature of the present invention that the blood flow channel surface 4 of the blood reservoir 1 of FIG. 1 is coated in part or as a whole by the polymer containing HEMA and MMA or in addition thereto by the block polymer represented by the above general formula (I) to prevent wettability by blood and the properties of preventing affixture of air bubbles.

With the blood flow channel surface 4 being thus coated with the polymer containing HEMA and MMA or further with the block copolymer represented by the above general formula (I) by way of a hydrophilizing treatment, the blood and the priming liquid introduced at the blood inlet port 2 is caused to flow smoothly on the blood flow channel surface 4 without becoming stagnant so that it flows smoothly on the gradually descending surface until it reaches the blood reservoir section 6. In this manner, the blood and the priming liquid are caused to flow quietly within the blood reservoir section 6 without any disturbances in the liquid flow or resultant foaming as in the prior art system.

The above described blood reservoir is provided within the excorporeal circulating blood circuit. However, it is preferably combined with an oxygenator and a heat exchanger to form an oxygenating device or system, as shown for example in FIG. 2.

In the embodiment shown in FIG. 2, the oxygenator 11 has a housing formed by a cylindrical main body of the housing 12 and attachment covers 13a, 13b closing both open ends of the main body of the housing 12. Within the entire region of the housing, a bundle of a multiplicity of hollow fibres 14 is arranged along the length of the housing so that the fibres are juxtaposed to and spaced apart from one another.

The both ends of the hollow fibres 14 are supported liquid-tightly against the main body of the housing 12 by partition walls 15a, 15b, with the opening ends of the fibres being not closed. A gas inflow space 16 formed by the attachment cover 13a, main body of the housing 12 and the partition wall 15 so as to be in communication with the inner space of the hollow fibres communicates in turn with a gas inflow port 17, and a gas outflow space 18 formed by the attachment cover 13b, main body of the housing 12 and the partition wall 15b so as to be in communication with the inner space of the hollow fibres communicates in turn with a gas outflow port 19b.

A blood chamber 20 defined by the inner wall of the main body of the housing 12, partition walls 15a, 15b and the outer walls of the hollow fibres 14 communicates with a blood inlet port 21 and a blood outlet port 22.

The oxygenator 11 shown herein is of the type in which gas exchange is performed with the oxygen-containing gas such as air being blown in the inner space of the hollow fibres 14 and with the blood being caused to flow on the outer sides of the hollow fibres 14.

The hollow fibres 14 may be formed of any suitable hydrophobic materials customarily used for oxygenators. For example, polytetrafluoroethylene, polypropylene or silicone is preferred.

According to the present invention, the outer wall 14a forming the blood flow channel surface of the hollow fibres 14 is preferably coated as a whole by the polymer containing HEMA and MMA or further with the block copolymer represented by the above general formula (I) and thereby hydrophilized to improve wettability thereof by blood.

The hollow fibre type oxygenators developed heretofore were generally of the type in which the blood is caused to flow within the interior of the hollow fibres. However, because of larger pressure losses encountered, the hollow fibre type oxygenators can be adapted only difficultly to pulsapile perfusion, separate excorporeal circulation or to blood cardioplegia.

The hollow fibre formed by a hydrophobic resin exhibits poor surface wettability by blood so that the blood is not permeated in to the space between the adjacent hollow fibres and an efficient gas exchange via the hollow fibres is obstructed with the result that sufficient gas exchange properties are not obtained. For wetting the outer wall surface of the hollow fibres, air bubbles remaining within the space between the hollow fibres need be removed by a laborious operation of imparting a physical shock to the oxygenator, such as by striking.

Thus, with the blood being caused to flow outside of the hollow fibres and the gas within the inner space of the fibres, pressure losses may be reduced, such that the blood can be supplied to the oxygenator and thence to the blood reservoir by the blood being taken out by the pressure head from the patient's body without the necessity of providing a blood delivery pump ahead of the oxygenator in the circulating circuit. Thus the oxygenator can be adapted to blood cardioplegia or separate excorporeal circulation.

To the blood outlet 22 of the oxygenator 11 is liquid-tightly connected the blood inlet port 2 of the blood reservoir 1 described with reference to FIG. 1.

A heat exchanger 23 is connected to the blood outlet of the oxygenator 11. The heat exchanger 23 includes a casing 24 in which a multiplicity of heat exchanger tubes 25 are arranged parallel to and at a spacing from one another along the length of the casing 24 The both ends of the heat exchanger tubes 25 are held liquid-tightly with respect to the side walls of the casing 24 by partition walls, not shown, with the opening ends of the tubes remaining open.

A spacing 26 defined by these partition walls, side walls of the casing 24 and the outer walls of the heat exchanger tubes 25 is kept in communication with a blood inlet port 27 and the blood inlet 21 to the oxygenator 11. The inner spacing of the heat exchanger tubes 25 liquid-tightly separated from the spacing 26 is kept in communication with a water inlet port 28 communicating with one of the partition walls of the casing 24 and a water outlet port, not shown, communicating with the outer sides of the other partition wall of the casing 24.

In the above described heat exchanger 23, the blood flows into the heat exchanger 23 via blood inlet port 27 to flow along the outer sides of the heat exchanger tubes 25, while warm or cold water flows in the inside of the heat exchanger tubes 25 from the water inlet port 28 to warm or chill the blood contacting with the heat exchanger tubes 15. However, it is also possible to use a heat exchanger of the type in which the blood flows in the inside of the heat exchanger tubes and the cooling or heating medium is caused to flow on the outer sides of the heat exchanger tubes.

In the oxygenating unit in which the blood reservoir 1 is integrated to the oxygenator 11 and the heat exchanger 23, the blood flowing into the inside of the heat exchanger 23 via the blood inlet port 27 is heated or chilled until it reaches the blood inlet 21 of the oxygenator 11. The blood flowing from the blood inlet 21 of the oxygenator 11 undergoes a gas exchange with the oxygen containing gas flowing in the inside space of the hollow fibre 14, as the blood flows through the blood chamber 20, so that excess carbon dioxide in the blood is removed, while oxygen is replenished to supplement consumed oxygen.

Preferably the overall surface of the outer wall 14a of the hollow fibres 14 acting as the blood flow channel surface is covered by the HEMA ot MMA containing polymer or further thereon the block polymer represented by the above general formula (I) and thereby hydrophilized to improve the wettability by the blood and the properties of preventing affixture of air bubbles, so that there is no risk for the fibers to be flocculated by the air to form so-called cavities as in the above described prior art system. In addition, the blood may flow smoothly into the blood chamber 20 without residing there so that the gas exchange may be performed efficiently.

The blood thus replenished with oxygen flows out at a blood outlet 22 of the oxygenator 11 to flow then into the blood reservoir 1 via the blood inlet 2 of the blood reservoir 1 communicating with the outlet 22. The blood introduced via the blood inlet 2 then reaches the blood influent section 25 contiguous to the blood inlet 2 to pass by the defoaming member 36 to flow smoothly on the blood flow channel surface 4 coated by the polymer containing HEMA and MMA or in addition thereto the block polymer of the formula (I) to flow down quietly and stored in the blood reservoir section 6 without forming air bubbles in the blood reservoir section 6. These effects in the blood reservoir 1 are most outstanding at the time of bloodless priming.

The blood thus stored in the blood reservoir section 6 without forming air bubbles is led out at the blood outlet 3 at the lower portion of the blood reservoir section 6 for blood delivery.

And due to improvement of adaptability to blood, it is expected that decrease of platelets is restrained.

It is noted that the description of the above embodiment has been made with reference to hollow fibres in an oxygenator. However, the present invention is not limited thereto but may also be applied to hollow fibres employed for example in hemoconcentrators.

In the blood filter shown in FIG. 3, the properties of preventing affixture of air bubbles and adaptability to blood are improved, as in the preceding embodiment. In addition, when the blood filter is processed with the block copolymer represented by the general formula (I), among the aforementioned polymers, wettability of the net-like filter material is improved to facilitate the priming operation.

Figure 5:
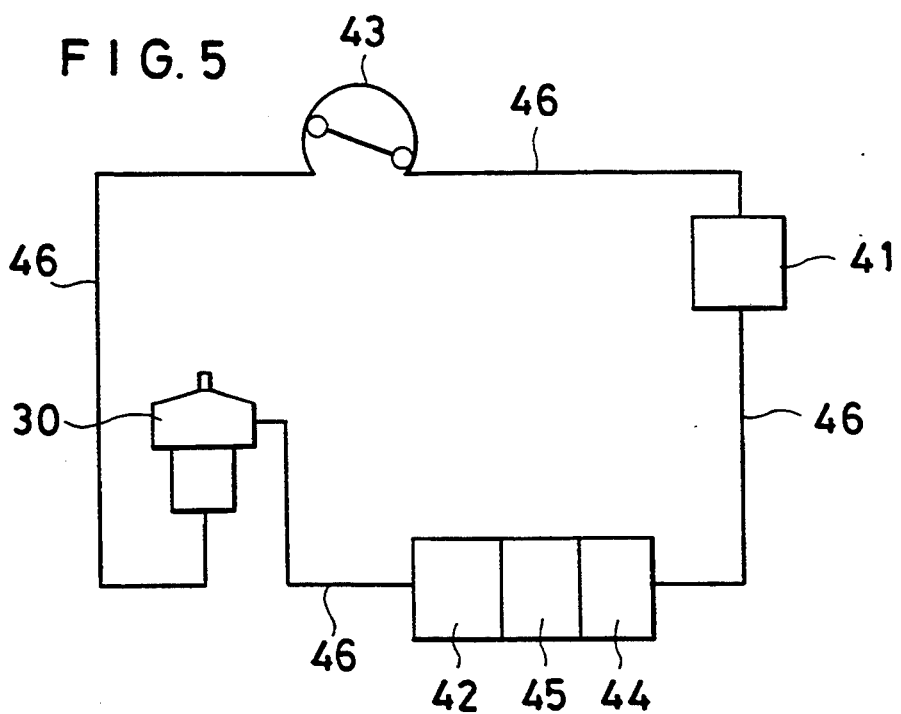

The same applies for the pump oxygenating circuit system shown in FIGS. 4 and 5.

EXAMPLES

The description with reference to certain Examples will be given hereinbelow for illustration of the present invention.

Examples for First Aspect of the Invention

Comparative Example

Using 34000 microporous polypropylene hollow fibres, each 300 microns in outside diameter, an oxygenator having a film or membrane area of 3.1 m2 was prepared.

Example 1

A 0.4% solution of $KM_nO_4$/conc. $H_2SO_4$ was charged into an oxygenator prepared similarly to the Comparative Example. While the narrow portion of the oxygenator was struck, the oxygenator was allowed to stand for five minutes, and the liquid inside the oxygenator was discharged. The oxygenator was washed with water and dried in air.

Example 2

2 liters of a 4% albumin solution was circulated in the oxygenator prepared similarly to Comparative Example at a rate of 2 liters per minute as the constricted portion of the oxygenator was struck. The oxygenator was then dried in air.

Example 3

A methanol solution containing 1 w/v % of PHEMA was charged into an oxygenator prepared in the same manner as in Comparative Example. While the constricted portion of the oxygenator was struck, the oxygenator was allowed to stand for one minute. After the liquid inside the oxygenator was discharged, the oxygenator was dried in air.

Example 4

Using a corona discharge unit HFS 202 produced by Kasuga Denki KK, the same hollow fibres of microporous polypropylene as those employed in Comparative Example, were taken up on a bobbin at a take-up speed of 50 m/min, while the current of 6.5 A at 120 V was caused to flow in an electrode 10 mm wide and 20 mm long, wound by a Teflon sheet 80 microns thick. Then, using these hollow fibres, an oxygenator similar to that used in the Comparative Example was assembled.

Example 5

The hollow fibres same as those used in the Comparative Example were cut to lengths of 50 cm and arrayed within a tank so as to avoid stacking. The fibres were then subjected to plasma processing at 100 W for two minutes at $10^{-1}$ torr and 30° to 40° C. Using the thus produced plasma processed hollow fibres, an oxygenator similar to that used in Comparative Example was prepared.

Example 6

After a gas port of an oxygenator prepared in the similar manner as in Comparative Example, ozone was introduced for ten minutes via a blood inlet port. Then, after ozone was similarly introduced via blood outlet port for ten minutes, the outer wall of the hollow fibre was subjected to a hydrophilizing treatment.

Test Example 1

The ability of oxygen addition of the oxygenators prepared in Comparative Example and Examples 1 to 6 was measured in accordance with AAMI standards. The results are shown in Table 1. With regard to the properties of the oxygenators shown in Table 1, the indications given below have the following meanings:

Before striking: The oxygen addition ability of the blood was measured immediately after priming of the oxygenator with the cow's blood.

After striking: The oxygen addition ability of the blood was measured after the constricted mid portion of the oxygenator was struck strongly with forceps as the blood was circulated after termination of the above priming.

TABLE 1

| | Ability of Oxygen Addition | |
|---|---|---|
| | Before Striking (%) | After Striking (%) |
| Comparative Example | 13 | 100 |
| Example 1 | 96 | 100 |
| Example 2 | 100 | 100 |
| Example 3 | 95 | 100 |
| Example 4 | 90 | 100 |
| Example 5 | 93 | 100 |
| Example 6 | 96 | 100 |

Test Example 2

Tests were conducted for measuring hydrophilic properties of the hollow fibres employed in oxygenators produced in Comparative Example and Examples 1 to 6. A beaker was filled with water and each one of the above hollow fibres was inserted into water from above orthogonally to the water surface. As a result, a meniscus was formed at the boundary between the outer wall of the hollow fibre and the liquid surface. In the case of fibres of the Comparative Example, the liquid surface was seen to be concave towards below along the outer wall of the hollow fibre, whereas, in the fibres of the Examples 1 to 6, the liquid surface was seen to rise along the outer wall of the fibre, thus indicating that hydrophilic properties were endowed to these fibres.

Examples For Second Aspect of the Invention

Comparative Example

A blood reservoir as shown in FIG. 1 was prepared by injection molding of a polycarbonate resin.

Example 1

After the blood flow channel surface of a blood reservoir prepared similarly to the Comparative Example was dipped for five minutes in a 0.4% $KM_nO_4$/conc. $H_2SO_4$, the liquid inside the reservoir was discharged and the reservoir was then washed with water and dried in air.

Example 2

A blood reservoir prepared in the similar manner to Comparative Example was filled with a 4% albumin solution and allowed to stand stationary for one minute. The liquid inside the blood reservoir was discharged and the blood reservoir was dried in air in a clean bench.

Example 3

A blood reservoir prepared in the similar manner to Comparative Example was filled with a methanol solution containing 0.2 w/v % of PHEMA and allowed to stand stationary. The liquid inside the blood reservoir was discharged and the blood reservoir was dried in air in a clean bench.

Example 4

Using a corona discharge unit HFS 202, produced by Kasuga Denki KK, the blood flow channel surface of a blood reservoir prepared in Comparative Example was subjected to a corona discharge treatment with the current of 5 A at 120 V being caused to flow in an electrode which is 10 mm wide and 20 mm long and which is wound by a Teflon sheet 80 microns thick.

Example 5

A blood reservoir produced in Comparative Example was subjected to plasma processing in a tank at 100 W for two minutes at a pressure of $10^{-1}$ torr and at a temperature of 30° to 40° C.

Example 6

A blood reservoir produced in Comparative Example was placed in a glass desiccator. After the temperature within the desiccator was set to 50° C., $O_2$ was caused to flow into an ozone generator at a flow rate of 0.8 liter per minute to produce ozone at 100 V, with the so-produced ozone being caused to flow into the desiccator. After this processing was carried out for 20 minutes, the inside space of the desiccator was replaced by $O_2$. The blood reservoir was then taken out of the desiccator to terminate the ozone processing.

Test Example 1

The blood flow channel surfaces of the blood reservoirs produced in accordance with the Comparative Example and Examples 1 to 6 were partially cut off to measure the contact angle with respect to water. The results are as shown in Table 2.

TABLE 2

| | Contact Angle (degrees) |
|---|---|
| Comparative Example | 92 |
| Example 1 | 40 |
| Example 2 | 33 |
| Example 3 | 39 |
| Example 4 | 49 |
| Example 5 | 65 |
| Example 6 | 62 |

Test Example 2

With 300 ml of physiological saline water being stored in blood reservoir sections of the blood reservoirs produced in Comparative Example and Examples 1 to 6, physiological saline water was caused to flow on the blood flow channel section at a flow rate of 4 liters per minute and the manner in which the physiological saline water flows on the blood channel surface and the generation of air bubbles in the blood reservoir sections were observed. The results are shown in Table 3.

TABLE 3

| | Blood Flow State | Foaming State at Blood Storage Section |
|---|---|---|
| Comparative Example | Two to three steak-like blood flows were observed | marked foaming |
| Example 1 | Blood flowed on the overall flow channel since it started to flow | no foaming |
| Example 2 | same as above | same as above |
| Example 3 | same as above | same as above |
| Example 4 | same as above | same as above |
| Example 5 | same as above | same as above |
| Example 6 | same as above | same as above |

EMBODIMENTS FOR THIRD AND FOURTH ASPECTS OF THE INVENTION

Example 1 and Comparative Examples 1 and 2

By way of Example 1, a 2% (methanol/methyl cellosolve=92/8) block copolymer of MMA (B segment)-/HEMA (A segment) was coated in the state of a solution on a microporous polypropylene flat film. Also, by way of Comparative Example 1, the above microporous polypropylene flat film was not subjected to any treatment such as hydrophilizing treatment. Finally, by way of Comparative Example 2, a 2% PHEMA solution in methanol was coated on a flat microporous polypropylene film to hydrophilize its surface. Using these films, the following tests on the properties were conducted.

i) Contact Angle

The contact angle of the surface of the polymer of Example 1 with respect to water was measured and found to be equal to 62°. After the polymer of Example 1 was allowed to stand in the polymer-coated state at room temperature for five days, the contact angle was again measured, and found to be substantially not changed.

The contact angle of the flat film of Comparative Example 1 with respect to water was about 109°, while that of the flat film of Comparative Example 2 was 64°. It has thus been shown that the above coating by the polymer results in the hydrophilized film.

ii) Tests on Ability to Expand Platelet

By way of tests on platelet spread ability test, the human blood was treated by a 1/10 vol. part of a 3.8% sodium citrate solution against coagulation and centrifuged for 15 minutes at 800 r.p.m. The supernatant was sampled and adjusted to a concentration of 60,000 per microliter by a diluent (physiological saline water/3.8% sodium citrate=9/1). The supernatant thus treated was dropped on film samples and allowed to stand for 30 minutes, after which the form and the number of the affixed platelets were checked.

In Example 1, the rates of affixture were 85%, 15% and 0% for types I,II and III, respectively, with the sum of the affixed platelets being 467/0.5 mm2. In Comparative Example 1, the rates were 49%, 23% and 28% for the types I, II and III, respectively, with the sum of the affixed platelets being 1386/0.5 mm2 and, in Comparative Example 2, the same rates were 30%, 25% and 45% for types I, II and III, respectively, with the sum of the affixed platelets being 1771/0.5 mm2.

It may be seen from this that coating the polymer of the Example in the above manner results not only in improved hydrophilic properties, but in improved blood adaptability.

The above classification into the types I, II and III has been made in accordance with the classification found in "Reaction of Platelets on the Surface of High Polymer Material for Medical Use" in "The Japanese Journal of Artificial Organs" 9(1), 228 to 231 (1980).

iii) Tests on Eluates

Tests on eluates were conducted in accordance with the disposable set standard for cardiopulmonary by-pass by the Ministry of Health and Welfare. Thus the circuit through which flowed the blood in the cardiopulmonary by-pass was filled with water which had been boiled and allowed to cool. Then, using a suitable tool, the ends of degasifying tubes, oxygen blowing tubes and connecting tubes were closed. The circuit was then heated at 70±1° C. for 30 minutes and cooled and the liquid contents were taken out as the test liquid and subjected to tests to be described later. The present oxygenator passed these tests.

The amount of consumption of potassium permanganate was within prescribed limits in Example 1, but exceeded the limits in Comparative Example 2.

Example 2 and Comparative Example 3

By way of Example 2, a polycarbonate blood reservoir as shown in FIG. 1 was prepared by injection molding and the blood flow channel surface thereof was coated with the block polymer of Example 1 by the same method as that of Example 1. The contact angle of the blood flow channel surface with respect to water was measured and found to be 38°.

On the other hand, a blood reservoir not coated with the polymer of Example 2 was similarly prepared by way of Comparative Example 3. The contact angle of the blood flow channel surface with respect to water was measured and found to be 91°.

The blood storage sections of the blood reservoirs of the Example 2 and the Comparative Example 3 were charged with 300 ml of physiological saline water and physiological saline water was caused to flow on the blood flow channel surfaces of the blood reservoirs to check for the manner in which the physiological saline water flowed on the blood flow channel surfaces and the manner in which the foam was generated in the blood storage sections.

It was now found that in the Example 2, the physiological saline water flowed uniformly and quietly on the blood flow channel surfaces in their entirety and no foam was seen to be generated in the blood storage sections. However, in Comparative Example 3, two main thick flows were seen approximately at the center of the blood flow channel surface with three fine meandering flows about the central flows, and air bubbles or foams were seen to be floating to and fro in the blood storage section. Example 3 and Comparative Example 4

By way of Example 3, an oxygenator was prepared with the use of 34000 microporous polypropylene hollow fibres of 300 μm in outside diameter, and a 2% (methanol/methylcellosolve=92/8) block copolymer solution of MMA (B segment)/HEMA (A segment) was charged in the oxygenator, which was allowed to stand for one minute while the constricted portion of the oxygenator was struck, the liquid contents in the oxygenator being then discharged and dried in air.

On the other hand, by way of Comparative Example 4, the same oxygenator was charged with a methanol solution containing 2 w/v % of PHEMA arid allowed to stand for one minute while the constricted portion of the oxygenator was struck, the liquid contents in the oxygenator being then discharged and dried in air.

The oxygenators of Example 3 and Comparative Example 4 were then subjected to tests on eluates in accordance with the disposable set standard for cardiopulmonary by-pass by the Ministry of Health and Welfare. Thus the circuit through which flowed the blood of the cardiopulmonary by-pass was filled with water which had been boiled and allowed to cool. Then, using a suitable tool, the ends of degasifying tubes, oxygen blowing tubes and connecting tubes were closed. The circuit was then heated at 70±1° C. for 30 minutes and cooled and the liquid contents were taken out as the test liquid and subjected to the following tests which the oxygenators under test must pass.

These tests include those on i) outward appearance and pH; ii) foaming; iii) degree of cleanliness; iv) lead and cadmiun; v) zinc; vi) a potassium permanganate reducing substance; and vii) evaporation residues.

In Example 3, the tested oxygenators were found to be within the reference standards for all of the tests. However, in Comparative Example 4, in the test for the potassium permanganate reducing substance, the consumption of potassium permanganate exceeded the reference standards.

Example 4

Using the blood filter shown in FIG. 3, the following tests were conducted. The housing of the blood filter was formed of polycarbonate, the filter medium was a polypropylene net having a mesh size of 380 meshes and the blood filtration area was 750 cm².

The blood filter was charged with a 1% methanol solution of MMA (B segment)/HEMA (A segment)-20/80 and dried in air immediately after the liquid contents were discharged.

The blood filter was then charged with an aqueous solution of a block polymer having the above formula (I) wherein (a+c)=75 and b=30 (Pluronic F-68 manufactured by BASF) and dried in air immediately after the liquid contents were discharged A priming liquid (physiological saline solution) was charged into the inside of the filter medium in the so-produced blood filter from the blood outlet. At this time, the priming liquid was accumulated in the inside of the filter medium until the filter medium was wetted. When the filter medium was wetted in this manner, the priming liquid stored in the inside of the filter medium was spurted out via the filter medium vigorously. The time elapsed since the charging of the priming liquid until ejection of the priming liquid out of the filter medium was measured. With the filter medium exhibiting poor wettability, the priming liquid was not discharged until a certain pressure drop was established with the progress of charging of the priming liquid.

The measured results are shown in the following Table 4.

TABLE 4

| Processing Method | remarks | Efflux Time Duration (seconds) | | |
|---|---|---|---|---|
| | | 1 | 10 | 20 |
| none | CX-AF | ************************* | | |
| polymer containing HEMA and MMA | 1.0% | ************* | | |
| poly(oxyethylene)-poly(oxypropylene) block polymer | 0.005% | ****** | | |
| polymer containing HEMA and MMA (1%) +poly (oxyethylene)-poly (oxypropylene) block polymer | 0.005% | ***** | | |

EFFECTS OF THE INVENTION

The oxygenator exhibits superior wettability by blood since the hollow fibres are hydrophilized by, for example, acid-, albumin-, PHEMA-, corona discharge-plasma- or ozone processing.

The result is that, since the air bubbles can be affixed only difficultly to the outer wall surfaces of the hollow fibres, the spaces between the fibers are not blocked by air bubbles and the blood may flow smoothly so that the gas exchange may be performed efficiently.

The blood reservoir of the present invention exhibits superior wettability by the priming liquid and the blood since the blood flow channel surface, above all, exhibits hydrophilic properties.

The result is that the blood flows down uniformly down the blood flow channel surface without flowing partially, so that it becomes possible to prevent air bubbles from being formed when the blood flows from the blood flow channel surface into the blood storage section.

The present invention provides a safe medical instrument which is hydrophilizingly treated by that at least the blood flow channel section of the instrument is coated by a polymer containing HEMA and MMA or in addition thereto a block polymer represented by the general formula (I) and thereby hydrophilized, and which also is superior in adaptability, to blood, so that the present invention may be applied extensively to hollow fibres or to blood reservoirs.

What is claimed is:

1. A hollow fiber oxygenator comprising
an elongated housing,
a bundle of hydrophobic porous hollow fibers comprised of a polyolefin resin and having inner and outer surfaces arranged within the housing in the elongated direction thereof whereby a chamber is formed between an inner surface of the housing and the outer surfaces of the porous hollow fibers,
blood inlet and outlet ports extending through the housing and communicating with the chamber,
partition walls supporting end portions of the hollow fibers and defining the length of the chamber, and
oxygen inlet and outlet ports communicating with the interior of the porous hollow fibers, wherein at least a portion of the outer surfaces of the porous hollow fibers is hydrophilized by coating the surfaces with a block copolymer containing hydroxyethyl methacrylate segments and methyl methacrylate segments.

2. The hollow fiber oxygenator according to claim 1 wherein said at least a portion of the outer surfaces is further coated with a poly(oxyethylene)poly(oxypropylene) block polymer represented by the formula:

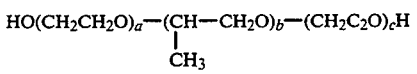

3. The hollow fiber oxygenator according to claim 2 wherein $2 \leq a+c \leq 500$ and $10 \leq b \leq 50$.

* * * * *

UNITED STATES PATENT AND TRADEMARK OFFICE
CERTIFICATE OF CORRECTION

PATENT NO. : 5,429,802
DATED : July 4, 1995
INVENTOR(S) : Kazuhiko HAGIWARA et al It is certified that error appears in the above-indentified patent and that said Letters Patent is hereby corrected as shown below:

On the title page add:

-- [30]      Foreign Application Priority Data
    Dec. 25, 1987 [JP]  Japan ............. 62-329159
    Dec. 25, 1987 [JP]  Japan ............. 62-329160
    Dec. 28, 1987 [JP]  Japan ............. 62-333660
    Nov. 28, 1988 [JP]  Japan ............. 63-300301 --.

In Column 1, line 36, delete "the, se" and insert -- these --.

In Column 1, line 45, delete "printing" and insert -- priming --.

In Column 2, line 61, after "liquid", insert -- will --.

In Column 3, line 43, delete "researche" and insert -- research --.

In Column 4, line 9, delete "exhibit" and insert -- exhibits --.

In Column 7, line 62, "Operation" should be a subheading on a separate line.

In Column 8, line 44, delete ",".

In Column 8, line 44, after "improved", insert -- . --.

In Column 9, line 16, delete "contents" and insert -- content --.

In Column 10, line 49, delete "or" and insert -- of --.

In Column 10, line 50, delete "How" and insert -- flow --.

In Column 12, line 16, delete "opening".

UNITED STATES PATENT AND TRADEMARK OFFICE
CERTIFICATE OF CORRECTION

PATENT NO. : 5,429,802
DATED : July 4, 1995
INVENTOR(S) : Kazuhiko HAGIWARA et al It is certified that error appears in the above-indentified patent and that said Letters Patent is hereby corrected as shown below:

In Column 16, line 2, delete "along-the" and insert -- along the --.

In Column 16, lines 42-43, delete "the-current" and insert -- the current --.

In Column 19, line 6, "Example 3 and Comparative Example 4" should be a subheading on a separate line.

In Column 19, line 18, delete "arid" and insert -- and --.

In Column 19, line 49, delete "meshes" and insert -- mesh --.

Signed and Sealed this

Eighteenth Day of June, 1996

Attest:

BRUCE LEHMAN

Attesting Officer

Commissioner of Patents and Trademarks